(12) United States Patent
Selent et al.

(10) Patent No.: US 7,217,828 B2
(45) Date of Patent: *May 15, 2007

(54) PHOSPHININE COMPOUNDS AND METAL COMPLEXES THEREOF

(75) Inventors: Detlef Selent, Berlin (DE); Armin Boerner, Rostock (DE); Renat Kadyrov, Rostock (DE); Cornelia Borgmann, Recklinghausen (DE); Dieter Hess, Marl (DE); Klaus-Diether Wiese, Haltern (DE); Dirk Roettger, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 161 days.

This patent is subject to a terminal disclaimer.

(21) Appl. No.: 10/911,499

(22) Filed: Aug. 5, 2004

(65) Prior Publication Data

US 2005/0043279 A1 Feb. 24, 2005

Related U.S. Application Data

(62) Division of application No. 09/989,077, filed on Nov. 21, 2001, now Pat. No. 6,818,770.

(30) Foreign Application Priority Data

Nov. 24, 2000 (DE) ............................... 100 58 383

(51) Int. Cl.
C07F 9/02 (2006.01)
(52) U.S. Cl. ............................ 556/19; 558/76; 558/78; 558/81; 568/455
(58) Field of Classification Search ................. 546/25, 546/334; 558/45, 75, 76, 78, 81; 549/335; 556/50, 46, 52, 19
See application file for complete search history.

(56) References Cited

U.S. PATENT DOCUMENTS

| | | | |
|---|---|---|---|
| 4,668,651 A | 5/1987 | Billig et al. | |
| 4,694,109 A | 9/1987 | Devon et al. | |
| 4,748,261 A | 5/1988 | Billig et al. | |
| 4,879,416 A | 11/1989 | Puckette et al. | |
| 4,885,401 A | 12/1989 | Billig et al. | |
| 5,093,534 A | 3/1992 | Ludwig et al. | |
| 5,312,996 A | 5/1994 | Packett | |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,331,657 B1 | 12/2001 | Kaizik et al. | |
| 6,403,836 B2 | 6/2002 | Kaizik et al. | |
| 6,403,837 B1 | 6/2002 | Hess et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Röttger et al. | |
| 6,627,782 B2 | 9/2003 | Kaizik et al. | |
| 6,680,414 B2 | 1/2004 | Knoop et al. | |
| 6,720,457 B2 | 4/2004 | Drees et al. | |
| 6,818,770 B2 * | 11/2004 | Selent et al. ................... | 546/25 |
| 6,924,389 B2 | 8/2005 | Jackstell et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,109,346 B2 | 9/2006 | Beller et al. | |
| 2003/0144559 A1 | 7/2003 | Hess et al. | |
| 2003/0195368 A1 | 10/2003 | Rottger et al. | |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2005/0171371 A1 | 8/2005 | Borner et al. | |
| 2005/0182277 A1 | 8/2005 | Totsch et al. | |
| 2005/0209455 A1 | 9/2005 | Boerner et al. | |
| 2005/0209489 A1 | 9/2005 | Moller et al. | |
| 2005/0234270 A1 | 10/2005 | Kaizik et al. | |
| 2005/0256281 A1 | 11/2005 | Grund et al. | |
| 2006/0036121 A1 | 2/2006 | Kaizik et al. | |
| 2006/0089469 A1 | 4/2006 | Komarov et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0183936 A1 | 8/2006 | Grass et al. | |

FOREIGN PATENT DOCUMENTS

| | | |
|---|---|---|
| DE | 196 02 301 | 7/1996 |
| EP | 0 155 508 | 9/1985 |
| EP | 0 214 622 | 3/1987 |
| EP | 0 247 595 | 12/1987 |
| EP | 0 472 071 | 2/1992 |
| WO | WO 9530680 | 11/1995 |

* cited by examiner

OTHER PUBLICATIONS

E. Ya. Levina, et al., Russian Journal of General Chemistry, vol. 60, No. 4, pp. 663-670. "1,2-Dihydro-1,2,Azaphosphorines from the Reactions of Phosphorus Trichloride and of Ethylphosphonous Dichloride with N-(2-Ethylhexylidene) Butylamine," Sep. 20, 1990.

Primary Examiner—Bernard Dentz
Assistant Examiner—Binta Robinson
(74) Attorney, Agent, or Firm—Oblon, Spivak, McClelland, Maier & Neustadt, P.C.

(57) ABSTRACT

Phosphinines of formula (I) can be combined with metal salts to prepare hydroformylation catalysts. The phosphinine complexes have two phosphorus centers that may be substituted with a variety of hetero atoms or alkyl substituents to modify the ligand characteristics of the phosphinine. Phosphinine metal complexes are employed under normal hydroformylation reaction conditions. The preparatory routes to the phosphinine ligands of formula (I) allow for their convenient synthesis.

25 Claims, No Drawings

PHOSPHININE COMPOUNDS AND METAL COMPLEXES THEREOF

BACKGROUND OF THE INVENTION

1. Field of the Invention

The present invention relates to phosphinines and metal complexes thereof, the preparation of the phosphinines and their use as ligands in catalytic reactions.

2. Discussion of the Background

The reaction of olefinic compounds, carbon monoxide and hydrogen in the presence of a catalyst to form aldehydes having one more carbon atoms is known as hydroformylation (oxo process). As catalysts in these reactions, use is frequently made of compounds of transition metals of group VIII of the Periodic Table of the Elements, in particular rhodium and cobalt compounds. Hydroformylation using rhodium compounds generally offers the advantage of higher selectivity compared to the cobalt-catalyzed reaction and is thus usually more economical. The rhodium-catalyzed hydroformylation is usually carried out using complexes comprising rhodium and preferably trivalent phosphorus compounds as ligands. Known ligands are, for example, compounds from the classes of phosphines, phosphites and phosphonites. A good review of the hydroformylation of olefins may be found in B. Cornils, W. A. Herrmann, "*Applied Homogeneous Catalysis with Organometallic Compounds*", Vol. 1&2, VCH, Weinheim, N.Y., 1996.

Each catalyst system (cobalt or rhodium) has its specific advantages. Different catalyst systems are therefore used depending on the starting material and target product, as the following examples show. If rhodium and triphenylphosphine are employed, α-olefins can be hydroformylated at relatively low pressures. An excess of triphenylphosphine is generally used as phosphorus-containing ligand, with a high ligand/rhodium ratio being necessary to increase the selectivity of the reaction in favor of the commercially desired n-aldehyde product.

DISCUSSION OF THE RELATED ART

The patents U.S. Pat. No. 4,694,109 and U.S. Pat. No. 4,879,416 describe bisphosphine ligands and their use in the hydroformylation of olefins at low synthesis gas pressures. High activities and high n/i-selectivities are achieved using ligands of this type, especially in the hydroformylation of propene. WO 95/30680 discloses bidentate phosphine ligands and their use in catalysis, including hydroformylation reactions. Ferrocene-bridged bisphosphines are described, for example, in the patents U.S. Pat. No. 4,169,861, U.S. Pat. No. 4,201,714 and U.S. Pat. No. 4,193,943 as ligands for hydroformylations. Our phosphines don't have bridging metals.

The disadvantage of bidentate phosphine ligands is the relatively high cost of preparing them. It is therefore often not economically viable to use such systems in industrial processes.

Rhodium-monophosphite complexes are suitable catalysts for the hydroformylation of branched olefins having internal double bonds, but the selectivity to terminally hydroformylated compounds is low. EP 0 155 508 discloses the use of bisarylene-substituted monophosphites in the rhodium-catalyzed hydro-formylation of sterically hindered olefins, e.g. isobutene.

Rhodium-bisphosphite complexes catalyze the hydroformylation of linear olefins having terminal and internal double bonds forming predominantly terminally hydroformylated products, while branched olefins having internal double bonds are reacted to only a small extent. Coordination of these ligands to a transition metal center gives catalysts of increased activity, but the operating life of these catalyst systems is unsatisfactory, among other things because of the hydrolysis sensitivity of the phosphite ligands. The use of substituted bisaryl diols as starting materials for the phosphite ligands, as described in EP 0 214 622 or EP 0 472 071, has enabled considerable improvements to be achieved.

According to the literature, the rhodium complexes of these ligands are extremely active hydroformylation catalysts for α-olefins. The patents U.S. Pat. No. 4,668,651, U.S. Pat. No. 4,748,261 and U.S. Pat. No. 4,885,401 describe polyphosphite ligands which allow α-olefins and also 2-butene to be converted with high selectivity into the terminally hydroformylated products. Bidentate ligands of this type have also been used for the hydroformylation of butadiene (U.S. Pat. No. 5,312,996).

Although the phosphinines mentioned are very good complexing ligands for rhodium hydroformylation catalysts, it is desirable to improve their effectiveness and stability still further.

SUMMARY OF THE INVENTION

An object of the present invention is to provide phosphinine complexes and methods for preparing phosphinine complexes.

Another object of the invention is to provide metal complexes containing phosphinine ligands and methods for preparing metal complexes of phosphinine ligands.

A further object of the invention is to provide methods for catalytic hydroformylation using phosphinine metal complexes.

DETAILED DESCRIPTION OF THE INVENTION

It has been found that phosphinines having the structure I

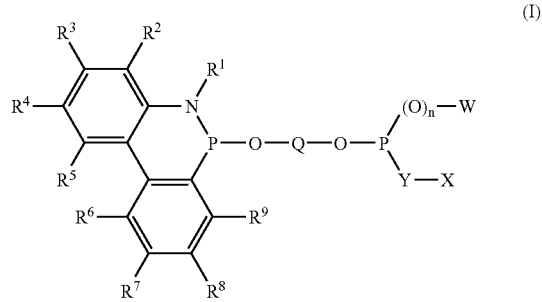

(I)

can be prepared simply and are suitable as ligands in metal-catalyzed reactions.

The present invention accordingly provides phosphinines of the formula I where n=0 or 1,

Y=O, NH, NR¹,

R¹=H, an aliphatic or aromatic hydrocarbon radical having from 1 to 25 carbon atoms, CH₃, R², R³, R⁴, R⁵, R⁶, R⁷, R⁸, R⁹=H, an aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, where R² to R⁹ are identical or different and may be covalently linked to one another, F, Cl, Br, I, —CF₃, —OR¹⁰, —COR¹⁰, —CO₂R¹⁰, —CO₂M, —SR¹⁰, —SO₂R¹⁰, —SOR¹⁰, —SO₃R¹⁰, —SO₃M, —SO₂NR¹⁰R¹¹, NR¹⁰R¹¹, N=CR¹⁰R¹¹, NH₂, R¹⁰, R¹¹=H, a substituted or unsubstituted, aliphatic or aromatic hydrocarbon radical having from 1 to 25 carbon atoms, identical or different, M=an alkali metal, alkaline earth metal, ammonium or phosphonium ion, Q=a divalent aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, W, X=aliphatic, alicyclic, aliphatic-alicyclic, heterocyclic, aliphatic-heterocyclic, aromatic, aliphatic-aromatic hydrocarbon radicals having from 1 to 50 carbon atoms, which may be identical or different or covalently linked to one another.

Specific embodiments of the phosphinines of the invention are phosphinines of the formulae II, III, IV and V

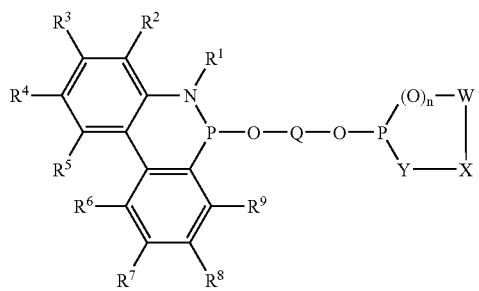

(II)

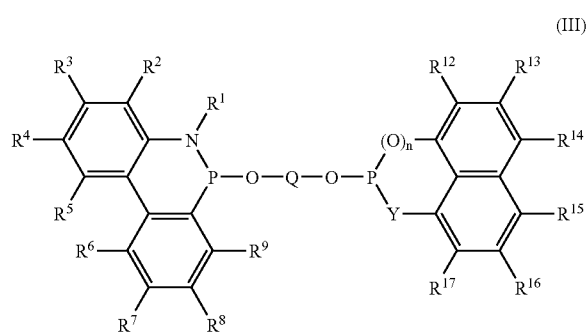

(III)

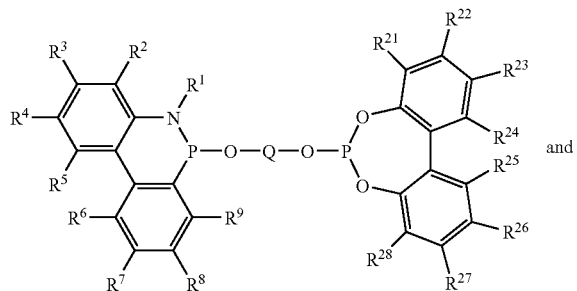

(IV)

and

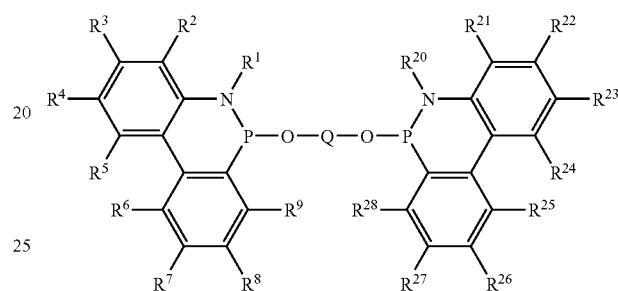

(V)

In the formula II, W and X are aliphatic, alicyclic, aliphatic-alicyclic, heterocyclic, aliphatic-heterocyclic, aromatic, aliphatic-aromatic hydrocarbon radicals, having from 1 to 50 carbon atoms, and X and W may be identical or different and may be covalently linked to one another. X and W in the formulae III, IV and V are the substituted or unsubstituted bisphenyl or naphthyl systems shown, Y is O, NH, NR¹, in particular oxygen, n is 0 or 1. The functional radicals R¹ to R³⁰ and Q have the following or abovementioned meanings.

In the formula III, R¹², R¹³, R¹⁴, R¹⁵, R¹⁶, R¹⁷ are H, an aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, where R¹² to R¹⁷ are identical or different and may be covalently linked to one another, F, Cl, Br, I, —CF₃, —OR¹⁸, —COR¹⁸, —CO₂R¹⁸, —CO₂M, —SR¹⁸, —SO₂R¹⁸, —SOR¹⁸, —SO₃R¹⁸, —SO₃M, —SO₂NR¹⁸R¹⁹, NR¹⁸R¹⁹, N=CR¹⁸R¹⁹, NH₂, M is an alkali metal, alkaline earth metal, ammonium or phosphonium ion.

R¹⁸ and R¹⁹ may be identical or different and are each H, methyl, t-butyl, a substituted or unsubstituted, aliphatic or aromatic hydrocarbon radical having from 1 to 25 carbon atoms.

In the formula IV:

R²¹, R²², R²³, R²⁴, R²⁵, R²⁶, R²⁷, R²⁸=H, an aliphatic, alicyclic, aliphatic-aliphatic heterocyclic, aliphatic-heterocyclic, aromatic, aromatic-aromatic, aliphatic-aromatic hydrocarbon radical having from 1 to 50 carbon atoms, where R²¹ to R²⁸ are identical or different and may be covalently linked to one another, F, Cl, Br, I, —CF₃, —OR²⁹, —COR²⁹, —CO₂R²⁹, —CO₂M, —SR²⁹, —SO₂R²⁹, —SOR²⁹, —SO₃R²⁹, —SO₃M, —SO₂NR²⁹R³⁰, NR²⁹R³⁰, N=CR²⁹R³⁰, NH₂, R²⁹, R³⁰=H, a substituted or unsubstituted, aliphatic or aromatic hydrocarbon radical having from 1 to 25 carbon atoms, M=an alkali metal, alkaline earth metal, ammonium or phosphonium ion,
Y is oxygen,
n is 1
and
$R^1$, $R^2$, $R^3$, $R^4$, $R^5$, $R^6$, $R^7$, $R^8$, $R^9$ and Q are as defined in claim 1, where $R^2$ to $R^9$ are identical or different and may be covalently linked to one another.

In the formula V, $R^{20}$ is H, $CH_3$, an aliphatic or aromatic hydrocarbon radical having from 1 to 25 carbon atoms,
$R^{21}$, $R^{22}$, $R^{23}$, $R^{24}$, $R^{25}$, $R^{26}$, $R^{27}$, $R^{28}$ are each H, an aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, where $R^{21}$ to $R^{28}$ are identical or different and may be covalently linked to one another,
F, Cl, Br, I, $-CF_3$, $-OR^{29}$, $-COR^{29}$, $-CO_2R^{29}$, $-CO_2M$, $-SR^{29}$, $-SO_2R^{29}$, $-SOR^{29}$, $-SO_3R^{29}$, $-SO_3M$, $-SO_2NR^{29}R^{30}$, $NR^{29}R^{30}$, $N=CR^{29}R^{30}$, $NH_2$,
$R^{29}$, $R^{30}$=H, a substituted or unsubstituted, aliphatic or aromatic hydrocarbon radical having from 1 to 25 carbon atoms,
M=an alkali metal, alkaline earth metal, ammonium or phosphonium ion,
Y is $NR^{20}$,
n is 0
and
$R^1$, $R^2$, $R^3$, $R^4$, $R^5$, $R^6$, $R^7$, $R^8$, $R^9$ and Q are as defined in claim 1, where $R^2$ to $R^9$ are identical or different and may be covalently linked to one another.

Examples of Q are divalent hydrocarbon radicals which may be aliphatic, alicyclic, aliphatic-alicyclic, heterocyclic, aliphatic-heterocyclic, aromatic or aliphatic-aromatic. Any ring systems present may in turn be substituted by the abovementioned hydrocarbon radicals. In open-chain structural elements, one or more methylene groups may be replaced by oxygen and/or sulfur and/or $NR^1$ and/or NH and/or one or more CH groups may be replaced by nitrogen.

Q is preferably a divalent radical containing an aromatic group or groups. Q can, for example, be a phenylene radical, a naphthylene radical, a divalent bisarylene radical or a divalent radical of a diphenyl ether. Furthermore, Q can have the structure —Ar—Z—Ar—. Here, Ar is a monocyclic or polycyclic divalent aromatic radical. Z is either a direct bond or a substituted or unsubstituted methylene group —$CR^{41}R^{42}$—, where $R^{41}$ and $R^{42}$ are hydrogen and/or aliphatic and/or aromatic radicals which have from 1 to 25 carbon atoms and may also contain hetero atoms. The radicals $R^{41}$ and $R^{42}$ may also be linked to form one or more rings, i.e. be covalently bonded to one another.

Among the phosphinines of the formulae I, II, III, IV and V, particular preference is given to those in which the radical Q is a hydrocarbon radical (bisarylene radical) of the formula VI

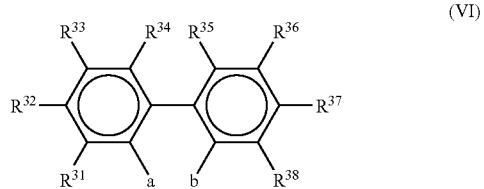

(VI)

where
$R^{31}$, $R^{32}$, $R^{33}$, $R^{34}$, $R^{35}$, $R^{36}$, $R^{37}$, $R^{38}$=H, an aliphatic, alicyclic, aliphatic-aliphatic, heterocyclic, aliphatic-heterocyclic, aromatic, aromatic-aromatic, aliphatic-aromatic hydrocarbon radical having from 1 to 50 carbon atoms,
F, Cl, Br, I, $-CF_3$, $-OR^{39}$, $-COR^{39}$, $-CO_2R^{39}$, $-CO_2M$, $-SR^{39}$, $-SO_2R^{39}$, $-SOR^{39}$, $-SO_3R^{39}$, $-SO_3M$, $-SO_2NR^{39}R^{40}$, $NR^{39}R^{40}$, $N=CR^{39}R^{40}$, $NH_2$,
$R^{39}$, $R^{40}$=H, a substituted or unsubstituted, aliphatic or aromatic hydrocarbon radical having from 1 to 25 carbon atoms,
M=an alkali metal, alkaline earth metal, ammonium or phosphonium ion, where the positions a and b are the points at which this substituent is linked into the structural element O-Q-O in the compounds of the formulae I, II, III, IV and V.

Examples of W and X are hydrocarbon radicals which may be aliphatic, alicyclic, aliphatic-alicyclic, heterocyclic, aliphatic-heterocyclic, aromatic, aromatic-aromatic or aliphatic-aromatic. Ring systems present in the radicals may in turn be substituted by the specified hydrocarbon radicals. In open-chain structural elements, one or more methylene groups may be replaced by oxygen and/or sulfur and/or $NR^1$ and/or NH, and/or one or more CH groups may be replaced by nitrogen.

The present invention also provides phosphinine-metal complexes comprising a metal of transition groups 4, 5, 6, 7 or 8 of the Periodic Table of the Elements and one or more phosphinines of the formulae I, II, III, IV and/or V. The substituents ($R^1$–$R^{42}$, Q, X, Y, n, W) of these phosphinines are as defined above.

Representative examples of ligands of the formulae I, II, III, IV and V according to the present invention are shown below, without the scope of the present invention being restricted thereby.

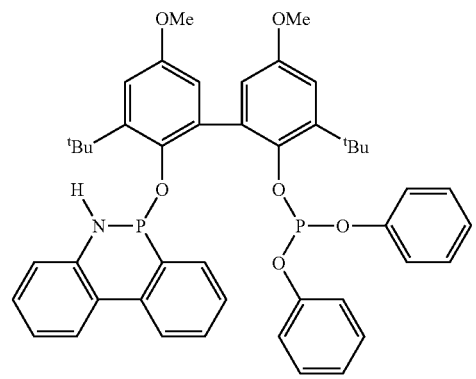

1-a

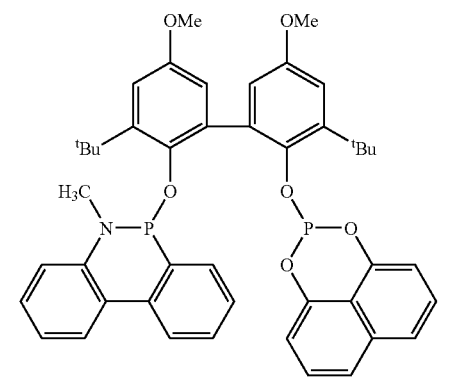

1-b

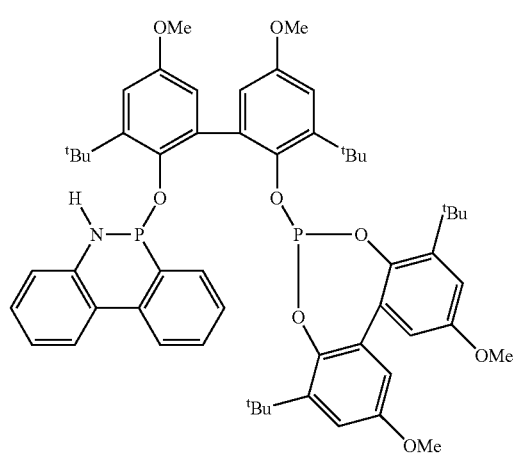
1-c
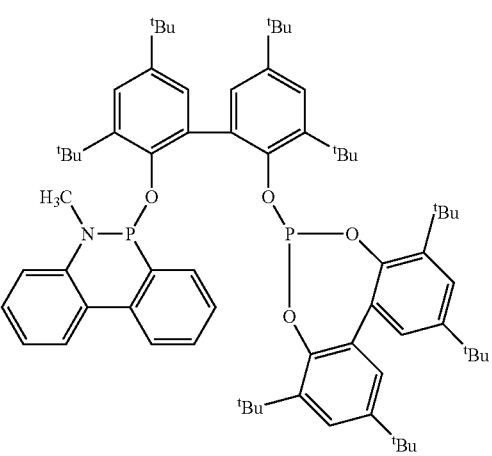
1-f
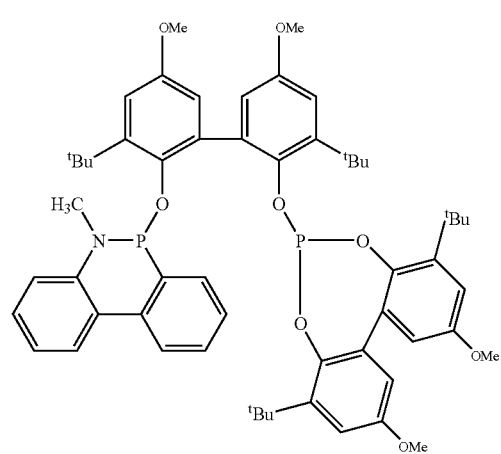
1-d
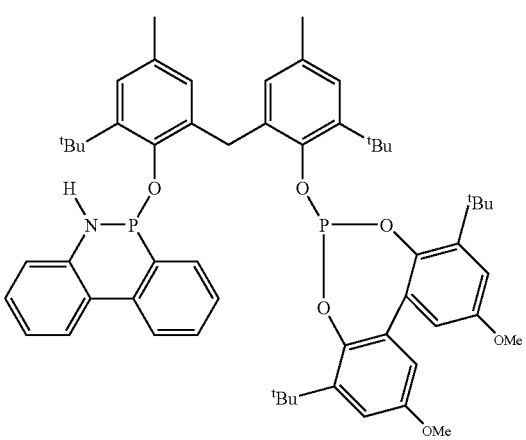
1-g
1-e
1-h 1-i

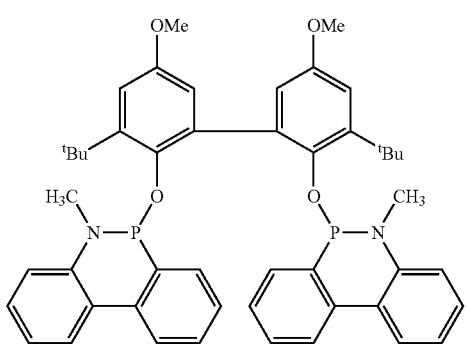

1-j

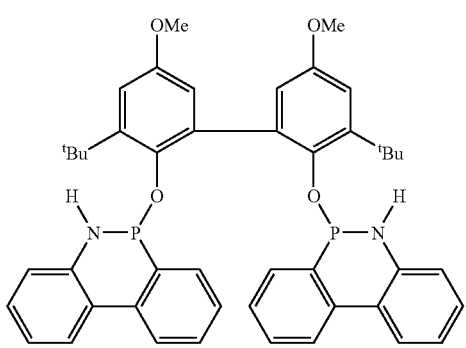

1-k

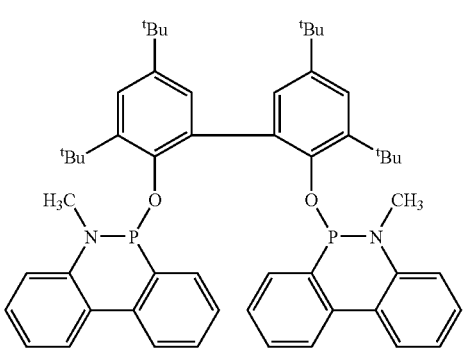

1-l

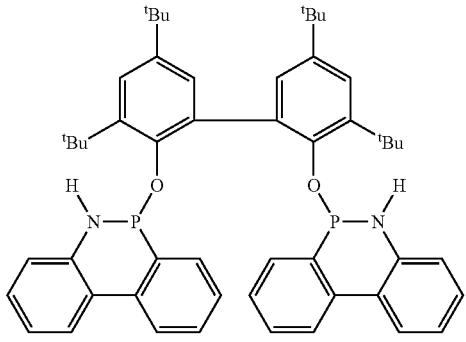

The phosphinines of the invention can be prepared by means of simple reactions. The basic procedure is illustrated by a route to compounds of the formula II:

1) A phosphorus trihalide, preferably phosphorus trichloride, is reacted with a diol or two molar equivalents of alcohol to form a monohalophosphite (intermediate A).

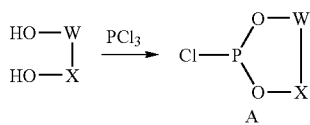

2) The intermediate A is reacted with a diol (HO—Q—OH) to give a hydroxyl-substituted phosphite (intermediate B).

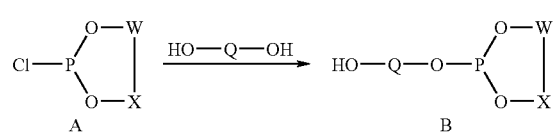

3) Intermediate B is reacted with the component C to give the desired bidentate ligand.

$$\begin{array}{c} R^3 \quad R^2 \\ R^4 \quad\quad\quad N{-}R^1 \\ \quad\quad\quad\quad P{-}Cl \quad + \\ R^5 \\ R^6 \quad\quad\quad R^9 \\ R^7 \quad R^8 \\ C \end{array}$$

$$HO{-}Q{-}O{-}P\begin{array}{c}O{-}W\\O{-}X\end{array} \longrightarrow II$$

B

The synthesis of compounds of type C is described in the literature. They can, for example, be obtained in a simple manner by reacting 2-aminobiphenylene with phosphorus trichloride in the presence of a Lewis acid catalyst.

The synthetic route to compounds of the formula II is only one of many possible routes, but demonstrates the basic procedure. An alternative route is, for example, reaction of C with the diol component and subsequent reaction with A to form the target product.

$$\begin{array}{c} R^3 \quad R^2 \\ R^4 \quad\quad\quad N{-}R^1 \\ \quad\quad\quad\quad P{-}Cl \quad \xrightarrow{HO-Q-OH} \\ R^5 \\ R^6 \quad\quad\quad R^9 \\ R^7 \quad R^8 \\ C \end{array}$$

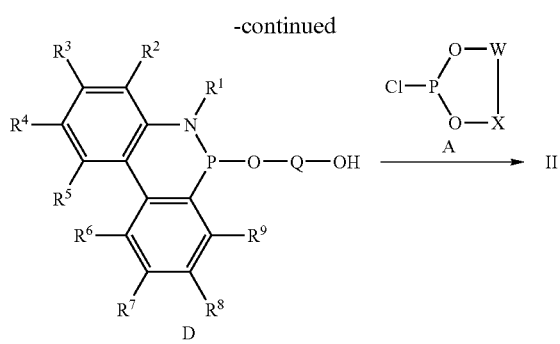

Since the diols used and their downstream products are frequently solid, the reactions are generally carried out in solvents. Solvents used are aprotic solvents which react neither with the diols nor with the phosphorus compounds. Examples of suitable solvents are tetrahydrofuran, diethyl ether and aromatic hydrocarbons such as toluene.

The reaction of phosphorus halides with alcohols forms a hydrogen halide which is bound by added bases. For example, tertiary amines such as triethylamine are used. It is sometimes also useful to convert the alcohols into metal alkoxides prior to the reaction, for example by reaction with sodium hydride or butyllithium.

The novel phosphinines of the formulae I, II, III, IV and V are suitable building blocks for the preparation of complexes with metals of transition groups 4, 5, 6, 7 or 8 of the Periodic Table of the Elements. Especially in the case of complexes with metals of transition group 8, these complexes can be used as catalysts for carbonylation reactions or hydroformylation reactions, e.g. for the hydro-formylation of $C_2$–$C_{25}$-olefins. The ligands have a high stability. High catalytic activities in hydroformylation reactions are obtained, particularly when using rhodium as catalyst metal. Owing to their high molecular weight, the phosphinines of the invention have a low volatility. They are therefore simple to separate from the more volatile reaction products. They are sufficiently soluble in customary organic solvents.

The invention additionally provides for the use of the phosphinines of the formulae I to V or of the corresponding phosphinine-metal complexes for the hydroformylation of olefins, preferably olefins having from 2 to 25 carbon atoms, to give the corresponding aldehydes.

Metals which are preferably used for preparing the catalytically active metal complexes of the phosphinines of the invention are rhodium, cobalt, platinum and ruthenium. The active catalyst is formed under the reaction conditions from the ligands of the invention and the metal. The ligands of the invention can be added in free form to the reaction mixture. It is also possible to use a transition metal complex containing the above-mentioned phosphinine ligands as precursor for the actual catalytically active complex. The hydroformylation process can be carried out using a stoichiometric amount or an excess (e.g. from 1:1 to 1:200 mol %/mol %) of free phosphinine ligands.

Furthermore, mixtures of various ligands, both the phosphinines of the invention and also other suitable phosphorus-containing ligands, can also be present as free ligand component.

As additional ligands in the reaction mixture, it is possible to use phosphines, phosphites, phosphonites or phosphinites. Examples of such ligands are:

Phosphines: triphenylphosphine, tris(p-tolyl)phosphine, tris (m-tolyl)phosphine, tris(o-tolyl)phosphine, tris(p-methoxyphenyl)phosphine, tris(p-dimethylaminophenyl)-phosphine, tricyclohexylphosphine, tricyclopentylphosphine, triethylphosphine, tri-(1-naphthyl)phosphine, tribenzylphosphine, tri-n-butylphosphine, tri-t-butylphosphine.

Phosphites: trimethyl phosphite, triethyl phosphite, tri-n-propyl phosphite, tri-1-propyl phosphite, tri-n-butyl phosphite, tri-1-butyl phosphite, tri-t-butyl phosphite, tris(2-ethylhexyl) phosphite, triphenyl phosphite, tris(2,4-di-t-butylphenyl) phosphite, tris(2-t-butyl-4-methoxyphenyl) phosphite, tris(2-t-butyl-4-methylphenyl) phosphite, tris (p-cresyl) phosphite. In addition, sterically hindered phosphite ligands as are described, inter alia, in EP 155 508, U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059, 710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP 472,071, EP 518, 241 and WO 97/20795 are also suitable ligands (the portions of each reference relevant to phosphine ligands is incorporated herein by reference).

Phosphonites: methyldiethoxyphosphine, phenyldimethoxyphosphine, phenyldiphenoxyphosphine, 2-phenoxy-2H-dibenz[c,e][1,2]oxaphosphorin and their derivatives in which all or some of the hydrogen atoms are replaced by alkyl radicals, aryl radicals or halogen atoms, and also ligands as described in WO/98 43935, JP 09-268152 and DE 198 10 794 and in the German patent applications DE 199 54 721 and DE 199 54 510 (the portions of each reference relevant to phosphonite ligands is incorporated herein by reference).

Customary phosphinite ligands are described, inter alia, in U.S. Pat. No. 5,710,344, WO 95/06627, U.S. Pat. No. 5,360,938 or JP 07082281 (the portions of each reference relevant to phosphonite ligands is incorporated herein by reference). Examples are diphenyl(phenoxy)phosphine and its derivatives in which all or some of the hydrogen atoms are replaced by alkyl radicals, aryl radicals or halogen atoms, diphenyl(methoxy)phosphine, diphenyl-(ethoxy) phosphine, etc.

Use is generally made of from 1 to 500 mol, preferably from 1 to 200 mol, more preferably from 3 to 50 mol, of the ligand of the invention per mole of group VIII transition metal. Fresh ligand can be added at any time during the reaction in order to keep the concentration of free ligand constant. The novel transition metal-phosphinine catalyst complexes can be synthesized before use. However, the catalytically active complexes are generally formed in situ in the reaction medium from a catalyst precursor and the phosphinine ligand of the invention.

Catalyst precursors used are salts or complexes of the transition metals. Examples are rhodium carbonyls, rhodium nitrate, rhodium chloride, $Rh(CO)_2(acac)$ (acac=acetylacetonate), rhodium acetate, rhodium octanoate and rhodium nonanoate.

The concentration of the metal in the reaction mixture is in the range from 1 ppm to 1000 ppm, preferably in the range from 5 ppm to 300 ppm.

The hydroformylation reaction carried out using the phosphinines of the invention or the corresponding metal complexes is carried out by known methods, as described, for example, in J. Falbe, "New Syntheses with Carbon Monoxide", Springer Verlag, Berlin, Heidelberg, N.Y., page 95 ff., (1980) (the portions thereof relevant to hydroformylation is incorporated herein by reference).

The reaction temperatures for a hydroformylation process using the novel phosphinines or phosphinine-metal complexes as catalyst are in the range from 40° C. to 180° C., preferably from 75° C. to 140° C. The pressures under which the hydroformylation proceeds are 1–300 bar of synthesis gas, preferably 15–64 bar. The molar ratio of hydrogen to carbon monoxide ($H_2/CO$) in the synthesis gas is from 10/1 to 1/10, preferably from 1/1 to 2/1.

The catalyst or the ligand is homogeneously dissolved in the hydroformylation mixture comprising starting material (olefins) and products (aldehydes, alcohols, high boilers formed in the process). An additional solvent can optionally be used.

The starting materials for the hydroformylation are monoolefins or mixtures of monoolefins having from 2 to 25 carbon atoms and a terminal or internal C—C double bond. They can be linear, branched or cyclic and can also have a plurality of olefinically unsaturated groups. Examples are propene, 1-butene, c-2-butene, t-2-butene, isobutene, butadiene, mixtures of C4-olefins, 1- or 2-pentene, 2-methyl-1-butene, 2-methyl-2-butene, 3-methyl-1-butene, 1-, 2- or 3-hexene, the C6-olefin mixture obtained in the dimerization of propene (dipropene), 1-heptene, heptenes, 2- or 3-methyl-1-hexene, 1-octene, octenes, 2-methylheptenes, 3-methylheptenes, 5-methyl-2-heptene, 6-methyl-2-heptene, 2-ethyl-1-hexene, the isomeric C8-olefin mixture obtained in the dimerization of butenes (dibutene), 1-nonene, nonenes, 2- or 3-methyloctenes, the C9-olefin mixture obtained in the trimerization of propene (tripropene), decenes, 2-ethyl-1-octene, dodecenes, the C12-olefin mixture obtained in the tetramerization of propene or the trimerization of butenes (tetrapropene or tributene), tetradecenes, hexadecenes, the 16-olefin mixture obtained in the tetramerization of butenes (tetrabutene) and also olefin mixtures prepared by cooligomerization of olefins having different numbers of carbon atoms (preferably from 2 to 4), optionally after fractional distillation to give fractions in which the component compounds have the same or a similar number of carbon atoms. It is likewise possible to use olefins or olefin mixtures produced by the Fischer-Tropsch synthesis, and also olefins which are obtained by oligomerization of ethene or are obtainable via metathesis reactions or a telomerization reaction.

Preferred starting materials are propene, 1-butene, 2-butene, 1-hexene, 1-octene, dimers and trimers of butene (dibutene, di-n-butene, diisobutene, tributene) and α-olefins in general.

The hydroformylation can be carried out continuously or batchwise. Examples of industrial apparatuses are stirred vessels, bubble columns, jet reactors, tube reactors and loop reactors, which may be connected to form a cascade and/or be provided with internals.

The reaction can be carried out in a single step or in a plurality of steps. The aldehyde compounds formed can be separated from the catalyst by a conventional method such as fractionation. This can, for example, be carried out industrially by means of a distillation, by means of a falling film evaporator or by means of a thin film evaporator. This is particularly applicable if the catalyst dissolved in a high-boiling solvent is separated from the lower-boiling products. The catalyst solution which has been separated off can be used for further hydroformylations. When using lower olefins (e.g. propene, butene, pentene), it is also possible to discharge the products from the reactor via the gas phase.

The following examples illustrate the invention but do not restrict its scope which is defined by the claims.

German application 100 58 383.0 filed on Nov. 24, 2000 is hereby incorporated in its entirety by reference.

In view of the teachings herein one of ordinary skill in the art can prepare the invention complexes and catalysts.

EXAMPLES

All preparations were carried out under protective gas using standard Schlenk techniques. The solvents were dried over suitable desiccants before use.

Example 1

Preparation of 10-chloro-9-methyl-9,10-dihydro-9-aza-10-phosphaphenanthrene

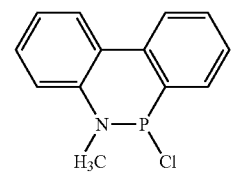

a) 2-Ethoxycarbonylaminobiphenyl

A solution of 21.7 g (0.2 mol) of ethyl chloroformate in 20 ml of dichloromethane is slowly added dropwise to a mixture of 25 g of 2-aminobiphenyl (0.148 mol) and 79 g of pyridine (1 mol) in 150 ml of dichloromethane while stirring. After stirring for 12 hours, 100 ml of 10% strength NaOH are added. The aqueous phase is separated off and shaken with dichloromethane. After the dichloromethane extract has been dried over sodium sulfate, the solvent is removed under reduced pressure and the red oil which remains is worked up by column chromatography (silica gel 60, 0.043 . . . 0.060 mm, eluant: hexane/ethyl acetate=9:1). Yield: 31.7 g=89%.

b) N-Methyl-o-phenylaniline

A solution of 18 g (0.075 mol) of 2-ethoxycarbonylaminobiphenyl in 100 ml of THF is added dropwise to a suspension of 14.2 g (0.373 mol) of lithium aluminum hydride in 300 ml of THF. The mixture is stirred for another 1 hour and then refluxed for 3 hours. Subsequently, while cooling in ice, 28 ml of water are firstly added dropwise and 18 ml of 15% strength aqueous sodium hydroxide are then added. After the precipitate has been separated off, it is washed a number of times with ether. The combined filtrates are dried over sodium sulfate, and the reddish liquid obtained after evaporation of the solvent is fractionated at 0.01 mbar. Bp.: 65–67° C. Yield: 10.64 g=77%.

c) 10-Chloro-9-methyl-9,10-dihydro-9-aza-10-phosphaphenanthrene (intermediate C1)

The cyclization of the amino compound with $PCl_3$ is carried out by a method analogous to that for the 9-H derivative: M. J. S. Dewar, V. P. Kubba, *J. Amer. Chem. Soc.* 1960, 82, 5685-5688 (the portion thereof relevant to the cyclization of the amino compound is incorporated herein by reference). 10 g (0.052 mol) of N-methylaminobiphenyl give 9 g=70% of the chloro compound. $^{31}$P-NMR: $(C_6D_6)$ δ 99.09 ppm.

Example 2

Synthesis of Intermediate B

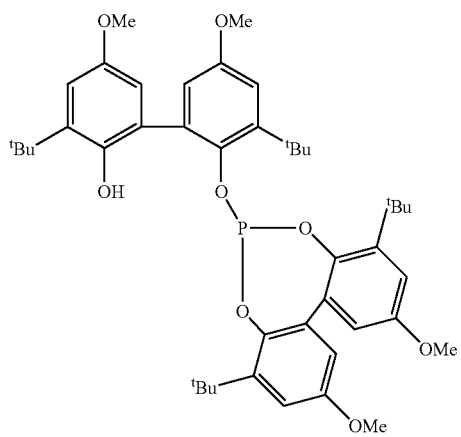

Intermediate B

A solution of 0.93 g of $PCl_3$ (6.75 mmol) in 10 ml of THF is added dropwise at 0° C. to a solution of 2.42 g of 2,2'-bis(6-tert-butyl-1-hydroxy-4-methoxyphenyl) (6.75 mmol) and 1.6 ml of pyridine in 22 ml of THF. After stirring for 4 hours at 25° C., the solvent is removed under reduced pressure. After addition of 40 ml of diethyl ether, filtration and evaporation under reduced pressure, 2.8 g (98%) of spectroscopically pure chlorophosphorous ester of 2,2'-bis (6-tert-butyl-1-hydroxy4-methoxyphenyl) are obtained: $^{31}$P-NMR $(CD_2Cl_2)$ δ 172.7 ppm. 2.8 g of this chloroester (6.62 mmol) in 20 ml of THF are added at room temperature to a monolithium phenoxide solution obtained at −20° C. from 2.37 g of 2,2'-bis(6-tert-butyl-1-hydroxy-4-methoxyphenyl) (6.62 mmol) in 30 ml of THF and 20.7 ml of a 0.32 M n-butyllithium solution in hexane (6.62 mmol). After 24 hours, the mixture is evaporated under reduced pressure. Addition of 40 ml of methylene chloride, filtration and removal of the solvent under reduced pressure give 4.6 g (93%) of highly viscous product.

Analysis (calculated for $C_{44}H_{57}O_8P=744.9$ g/mol):

C 70.35 (70.95); H 7.86 (7.71). $^{31}$P-NMR $(CD_2Cl_2)$ δ 140.7 ppm. $^1$H-NMR $(CD_2Cl_2)$ δ 1.43 (s, 9H); 1.56 (s, 9H); 1.63 (s, 9H); 1.67 (s, 9H); 4.01(s,3H); 4.03 (s, 6H); 4.05 (s, 3H); 5.42 (s, 1H); 6.7 . . . 7.3 (m, 8H) ppm. FAB MS: m/e 745 (37%, M+); 387 (100%, M$^+$ $^-$2,2'-bis(6-tert-butyl-1-hydroxy-4-methoxyphenyl)). IR ($CHCl_3$, 0.1 mm $CaF_2$), ν (OH)=3549 cm$^{-1}$.

Example 3

Synthesis of a Phosphinine of the Formula 1-c

One equivalent of n-butyllithium dissolved in 13 ml of hexane is added dropwise at −20° C. to 3.06 g of intermediate B from Example 2 (4.11 mmol) in 32 ml of THF while stirring. After warming to room temperature and stirring for 30 minutes, the solution obtained is added to 0.961 g of 10-chloro-9,10-dihydro-9-aza-10-phosphaphenanthrene (intermediate C-2 from Example 4) (4.11 mmol) dissolved in 7 ml of THF and the mixture is stirred at room temperature for 4 hours. The residue obtained after taking off the solvent mixture under reduced pressure is triturated in 80 ml of hexane. The mixture is filtered and the residue on the frit is extracted by distillation 5 times from the mother liquor. Evaporation of the solution to 50% of its original volume and storage at −28° C. for 3 days gives the crude product, which is recrystallized once more from hot hexane. Yield: 1.9 g=48%.

Analysis (calculated for $C_{56}H_{65}O_8P_2N=942.07$ g/mol): C 71.50 (71.40); H 7.25 (6.95); N 1.56 (1.47) %. $^{31}$P-NMR $(CD_2Cl_2)$: δ 82.55; 87.1; 139.0; 142.7. Diastereomer ratio=3.3:1. $^1$H-NMR $(CD_2Cl_2)$: δ 0.91 . . . 1.44 (36H); 3.74 . . . 3.85 (12H), 4.88 . . . 5.08 (1H); 6.51 . . . 8.1 (16H). FAB-MS: m/e 942 (7%, M+); 746 (26%); 539 (21%); 388 (37%); 199 (100%).

Example 4

Preparation of 10-chloro-9,10-dihydro-9-aza-10-phosphaphenanthrene

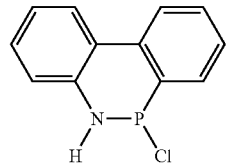

C-2

This compound was prepared as described by M. J. S. Dewar, V. P. Kubba, *J. Amer. Chem. Soc* 1960, 82, 5685–5688 (p. 20, line 19) and is hereinafter referred to as "C-2". The portion thereof relevant to the synthesis of "C-2" is incorporated herein by reference.

Example 5

Synthesis of a Phosphine of the Formula 1-e

One equivalent of n-butyllithium dissolved in 8 ml of hexane is added dropwise at −20° C. to 1.85 g of intermediate B from Example 2 (2.49 mmol) in 20 ml of THF while stirring. After warming to room temperature and stirring for 30 minutes, the solution obtained is added to 0.616 g of 10-chloro-9-methyl-9,10-dihydro-9-aza-10-phosphaphenanthrene (intermediate C-1 from Example 1) (2.49 mmol) dissolved in 5 ml of THF and the mixture is stirred at room temperature for 4 hours. The residue obtained after taking off the solvent under reduced pressure is triturated in 40 ml of hexane. The mixture is filtered and the residue on the frit is extracted by backdistillation 5 times from the mother liquor. Allowing to stand at room temperature for a number of days gives a white precipitate which is filtered off, washed with 10 ml of hexane and dried under reduced pressure at a bath temperature of 70° C. Yield: 1.99 g=84%. Analysis (calculated for $C_{57}H_{67}O_8P_2N=956$ g/mol): C 72.02 (71.61); H 7.69 (7.06); P 6.48 (5.99); N 1.39 (1.46). $^{31}$P-NMR ($CD_2Cl_2$): δ 101.2, 102.2; 141.7; 144.7. Diastereomer ratio=7.5:1. $^1$H-NMR ($CD_2Cl_2$): δ 0.9 . . . 1.45 (36H); 3.18 . . . 3.43 (3H); 3.74 . . . 3.94 (12H), 6.14 . . . 8.15 (16H). Cl-MS m/e 956 (10%, M$^+$); 745 (100%).

Examples 6 and 7

Hydroformylation of 1-octene

The experiment was carried out in a 200 ml stainless steel autoclave from Buddeberg, Mannheim, which was provided with a sparging stirrer, pressure pipette and pressure regulator, was installed in a thermostated oil bath and had previously been charged under protective gas. To minimize any influence of moisture and oxygen, the toluene used as solvent was dried using sodium ketyl and distilled under argon. The 1-octene used as substrate was refluxed over sodium for a number of hours and distilled under argon.

The autoclave was charged with 27 ml of toluene in which 5.456 mg=0.0176 mmol of [acacRh(COD)] and 0.088 mmol of the respective ligand had been dissolved. The Rh/P ratio was thus 1:10. 24 ml=about 16.8 g (149.3 mmol) of 1-octene were placed in the pressure pipette above the reactor. The Rh/1-octene ratio was thus about 1:8500. Reactor and pressure pipette were supplied via a bypass connected in parallel to the pressure regulation section with 33 bar of $CO/H_2$ (1:1; synthesis gas) for an intended pressure of 50 bar, or with 13 bar of $CO/H_2$ for an intended pressure of 20 bar, and the contents of the reactor were heated to 100° C. while stirring magnetically with the sparging stirrer at 1500 min$^{-1}$. After the intended temperature had been reached, the pressure was increased to 47 bar (17 bar) and the olefin mixture was injected from the pressure pipette into the reactor by means of a pressure of 55 bar (25 bar). An initial reaction pressure of 49.6 bar (19.2 bar) was established. After careful manual regulation to 50 bar (20 bar), the bypass was closed and the pressure was kept constant over the entire reaction time by means of the pressure regulator. The experiment was stopped after the chosen reaction time had expired by forced cooling. The reaction solution was taken out under protective gas and analyzed by gas chromatography.

The following table shows the results obtained using the individual ligands.

| Example | Ligand | Temp. [° C.] | p [bar] | t [h] | Yield [%] | Proportion of nonanal [%] |
|---|---|---|---|---|---|---|
| 6 | 1-c | 100 | 50 | 3 | 70 | 94.3 |
| 7 | 1-e | 100 | 20 | 3 | 49 | 93.6 |

Examples 8 and 9

Hydroformylation of a Mixture of 1-Octene, 2-Octene, 3-Octene and 4-Octene

The experiment was carried out in a 200 ml stainless steel autoclave from Buddeberg, Mannheim, which was provided with a sparging stirrer, pressure pipette and pressure regulator, was installed in a thermostated oil bath and had previously been charged under protective gas. To minimize any influence of moisture and oxygen, the toluene used as solvent was dried using sodium ketyl and distilled under argon. The octene isomer mixture used as substrate was refluxed over sodium for a number of hours and distilled under argon. Composition: 1-octene, 3.3%; cis+trans-2-octene, 48.5%; cis+trans-3-octene, 29.2%; cis+trans-4-octene, 16.4%; branched C8-olefins, 2.6%.

The autoclave was charged with 41 ml of toluene in which 18.75 mg=0.0604 mmol of [acacRh(COD)], the respective bidentate ligand and the coligand CL1 depicted below had been dissolved. The Rh/bidentate ligand (ligand)/ether phosphonite (coligand) ratio is shown in the table. 15 ml=10.62 g (94.63 mmol) of octenes were placed in the pressure pipette above the reactor. The ratio of Rh/octenes was thus about 1:1570. Reactor and pressure pipette were supplied via a bypass connected in parallel to the pressure regulation section with 13 bar of $CO/H_2$ (1:1; synthesis gas) and the contents of the reactor were heated to 130° C. while stirring magnetically with the sparging stirrer at 1500 min$^{-1}$. After the intended temperature had been reached, the pressure was increased to 17 bar and the olefin mixture was injected from the pressure pipette into the reactor by means of a pressure of 25 bar. An initial reaction pressure of 19.2 bar was established. After careful manual regulation to 20 bar, the bypass was closed and the pressure was kept constant over the entire reaction time by means of the pressure regulator. The experiment was stopped after three hours by forced cooling. The reaction solution was taken out under protective gas and analyzed by gas chromatography.

The following table shows the results obtained using the individual ligands.

| Example | Ligand/ Coligand | T [° C.] | Rh/Lig/Colig/olefin [mol/mol/mol/mol] | t [h] | Yield [%] | Proportion of nonanal [%] |
|---|---|---|---|---|---|---|
| 8 | 1-c/CL-1 | 130 | 1/2.5/5/1570 | 6 | 36 | 75.6 |
| 9 | 1-e/CL-1 | 130 | 1/2.5/5/1570 | 6 | 81 | 33.6 |

Coligand used

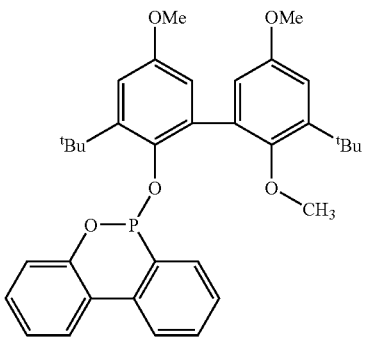

CL-1

The invention claimed is:

1. A phosphinine compound of formula I

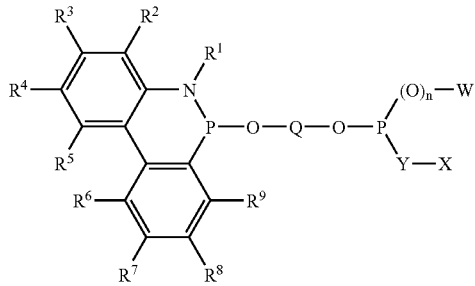

where
n=0 or 1,
Y=O, NH, NR$^1$,
R$^1$=H, an aliphatic or aromatic hydrocarbon radical having from 1 to 25 carbon atoms,
R$^2$, R$^3$, R$^4$, R$^5$, R$^6$, R$^7$, R$^8$, R$^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$^2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$, wherein at least one of R$^2$ to R$^9$ is heterocyclic or aliphatic heterocyclic,
R$^{10}$, R$^{11}$=H, a substituted or unsubstituted aliphatic or aromatic hydrocarbon radical having from 1 to 25 carbon atoms, identical or different,
M=an alkali metal, an alkaline earth metal, ammonium or phosphonium ion,
Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and
W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

2. A phosphinine compound of formula I

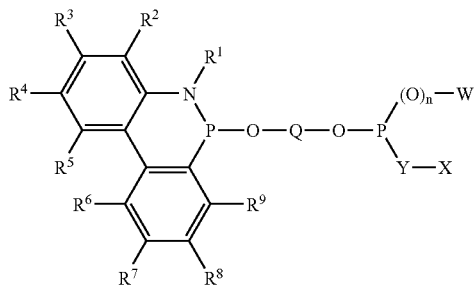

where
n=0 or 1,
Y=O, NH, NR$^1$,
R$^1$=H, an aliphatic or aromatic hydrocarbon radical having from 1 to 25 carbon atoms,
R$^2$, R$^3$, R$^4$, R$^5$, R$^6$, R$^7$, R$^8$, R$^9$ =H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$,
R$^{10}$, R$^{11}$=H, a substituted or unsubstituted aliphatic or aromatic hydrocarbon radical having from 1 to 25 carbon atoms, identical or different,
M=an alkali metal, an alkaline earth metal, ammonium or phosphonium ion,
Q=a heterocyclic or aliphatic-heterocyclic radical having from 1 to 50 carbon atoms, and
W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

3. A phosphinine compound of formula I

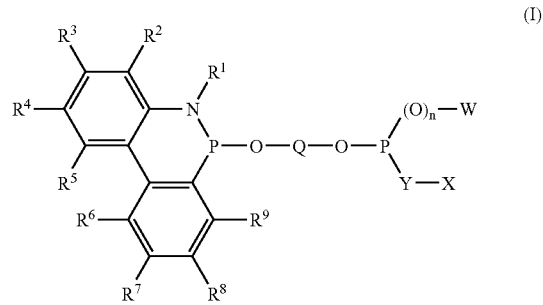

where
n=0 or 1,
Y=O, NH, NR$^1$,
R$^1$=H, an aliphatic or aromatic hydrocarbon radical having from 1 to 25 carbon atoms,
R$^2$, R$^3$, R$^4$, R$^5$, R$^6$, R$^7$, R$^8$, R$^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$,
R$^{10}$, R$^{11}$=H, a substituted or unsubstituted aliphatic or aromatic hydrocarbon radical having from 1 to 25 carbon atoms, identical or different,
M=an alkali metal, an alkaline earth metal, ammonium or phosphonium ion,
Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each a heterocyclic or aliphatic-heterocyclic radical having from 1 to 50 carbon atoms, which may be identical or different or covalently linked to one another.

4. The phosphinine compound as claimed in claim 1, wherein Q is a hydrocarbon radical of formula VI

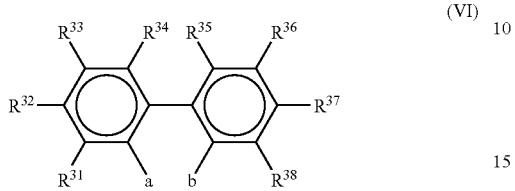

(VI)

where $R^{31}$, $R^{32}$, $R^{33}$, $R^{34}$, $R^{35}$, $R^{36}$, $R^{37}$, $R^{38}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, F, Cl, Br, I, —$CF_3$, —$OR^{39}$, —$COR^{39}$, —$CO_2R^{39}$, —$CO_2M$, —$SR^{39}$, —$SO_2R^{39}$, —$SOR^{39}$, —$SO_3R^{39}$, —$SO_3M$, —$SO_2NR^{39}R^{40}$, —$NR^{39}R^{40}$, N=$CR^{39}R^{40}$ or $NH_2$, $R^{39}$, $R^{40}$=H, a substituted or unsubstituted, aliphatic or aromatic hydrocarbon radical having from 1 to 25 carbon atoms, identical or different, M=an alkali metal, an alkaline earth metal, ammonium or phosphonium ion, and positions a and b serve as linkage points.

5. The phosphinine compound as claimed in claim 3, wherein Q is a hydrocarbon radical of formula VI

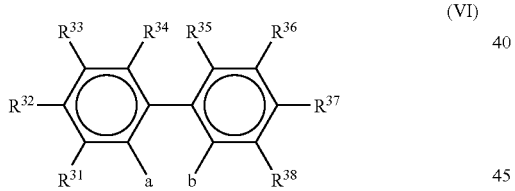

(VI)

where $R^{31}$, $R^{32}$, $R^{33}$, $R^{34}$, $R^{35}$, $R^{36}$, $R^{37}$, $R^{38}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, F, Cl, Br, I, —$CF_3$, —$OR^{39}$, —$COR^{39}$, —$CO_2R^{39}$, —$CO_2M$, —$SR^{39}$, —$SO_2R^{39}$, —$SOR^{39}$, —$SO_3R^{39}$, —$SO_3M$, —$SO_2NR^{39}R^{40}$, —$NR^{39}R^{40}$, N=$CR^{39}R^{40}$ or $NH_2$, $R^{39}$, $R^{40}$=H, a substituted or unsubstituted, aliphatic or aromatic hydrocarbon radical having from 1 to 25 carbon atoms, identical or different, M=an alkali metal, an alkaline earth metal, ammonium or phosphonium ion, and positions a and b serve as linkage points.

6. A phosphinine-metal complex comprising a metal of transition metal elements of Groups 4, 5, 6, 7 and 8 of the Periodic Table of the Elements and at least one phosphinine of formula I

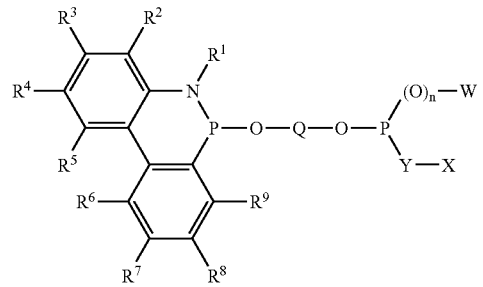

(I)

where n=0 or 1,

Y=O, NH, $NR^1$, $R^1$=H, an aliphatic or aromatic hydrocarbon radical having from 1 to 25 carbon atoms, $R^2$, $R^3$, $R^4$, $R^5$, $R^6$, $R^7$, $R^8$, $R^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where $R^2$ to $R^9$ are identical or different and may be covalently linked to one another, F, Cl, Br, I, —$CF_3$, —$OR^{10}$, —$COR^{10}$, —$CO_2R^{10}$, —$CO_2M$, —$SR^{10}$, —$SO_2R^{10}$, —$SOR^{10}$, —$SO_3R^{10}$, —$SO_3M$, —$SO_2NR^{10}R^{11}$, —$NR^{10}R^{11}$, N=$CR^{10}R^{11}$ or $NH_2$, wherein at least one of $R^2$ to $R^9$ is heterocyclic or aliphatic heterocyclic, $R^{10}$, $R^{11}$=H, a substituted or unsubstituted aliphatic or aromatic hydrocarbon radical having from 1 to 25 carbon atoms, identical or different, M=an alkali metal, an alkaline earth metal, ammonium or phosphonium ion, Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

7. A phosphinine-metal complex comprising a metal of transition metal elements of Groups 4, 5, 6, 7 and 8 of the Periodic Table of the Elements and at least one phosphinine of formula I

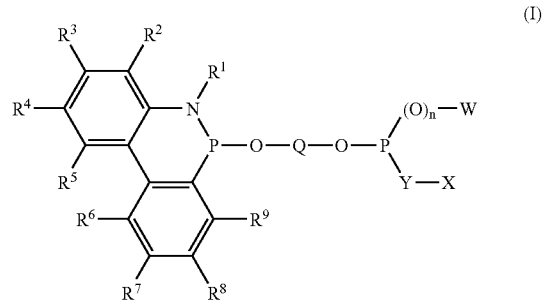

(I)

where
n=0 or 1,
Y=O, NH, NR$^1$,
R$^1$=H, an aliphatic or aromatic hydrocarbon radical having from 1 to 25 carbon atoms,
R$^2$, R$^3$, R$^4$, R$^5$, R$^6$, R$^7$, R$^8$, R$^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$,
R$^{10}$, R$^{11}$=H, a substituted or unsubstituted aliphatic or aromatic hydrocarbon radical having from 1 to 25 carbon atoms, identical or different,
M=an alkali metal, an alkaline earth metal, ammonium or phosphonium ion,
Q=a heterocyclic or aliphatatic heterocyclic radical having from 1 to 50 carbon atoms, and
W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

8. A phosphinine-metal complex comprising a metal of transition metal elements of Groups 4, 5, 6, 7 and 8 of the Periodic Table of the Elements and at least one phosphinine of formula I

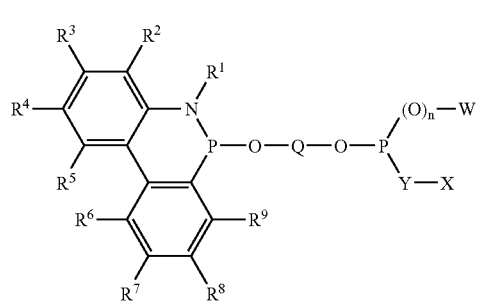

(I)

where
n=0 or 1,
Y=O, NH, NR$^1$,
R$^1$=H, an aliphatic or aromatic hydrocarbon radical having from 1 to 25 carbon atoms,
R$^2$, R$^3$, R$^4$, R$^5$, R$^6$, R$^7$, R$^8$, R$^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$,
R$^{10}$, R$^{11}$=H, a substituted or unsubstituted aliphatic or aromatic hydrocarbon radical having from 1 to 25 carbon atoms, identical or different,
M=an alkali metal, an alkaline earth metal, ammonium or phosphonium ion,
Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and
W and X are each a heterocyclic or aliphatic-heterocyclic radical having from 1 to 50 carbon atoms, which may be identical or different or covalently linked to one another.

9. The phosphinine-metal complex as claimed in claim 6, wherein W and X are each an aliphatic, alicyclic, aliphatic-alicylic, heterocyclic, aliphatic-heterocyclic, aromatic or aliphatic-aromatic hydrocarbon radical having from 1 to 50 carbon atoms and are covalently linked as in formula II

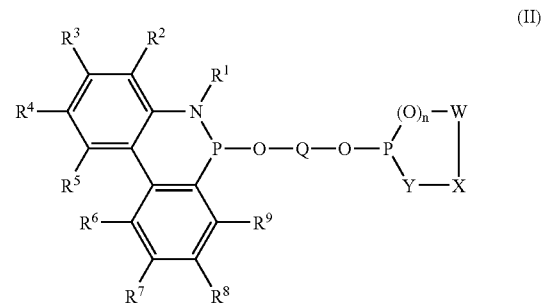

(II)

10. The phosphinine-metal complex as claimed in claim 7, wherein W and X are each an aliphatic, alicyclic, aliphatic-alicylic, heterocyclic, aliphatic-heterocyclic, aromatic or aliphatic-aromatic hydrocarbon radical having from 1 to 50 carbon atoms and are covalently linked as in formula II

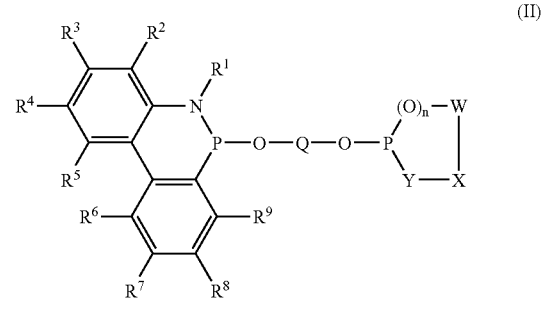

(II)

11. The phosphinine-metal complex as claimed in claim 6, wherein W and X are each an aromatic hydrocarbon radical having from 1 to 50 carbon atoms and are covalently linked as in formula III

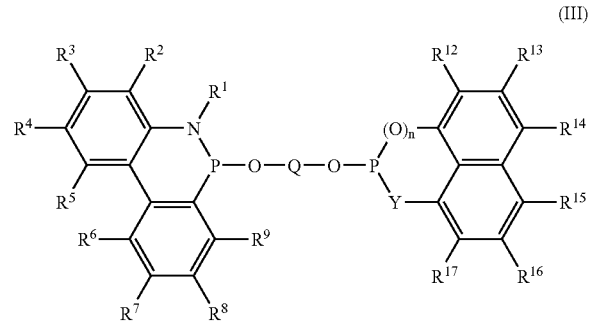

(III)

where
- $R^{12}$, $R^{13}$, $R^{14}$, $R^{15}$, $R^{16}$, $R^{17}$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where $R^{12}$ to $R^{17}$ are identical or different and may be covalently linked to one another, F, Cl, Br, I, —$CF_3$, —$OR^{18}$, —$COR^{18}$, —$CO_2R^{18}$, —$CO_2M$, —$SR^{18}$, —$SO_2R^{18}$, —$SOR^{18}$, —$SO_3R^{18}$, —$SO_3M$, —$SO_2NR^{18}R^{19}$, —$NR^{18}R^{19}$, $N{=}CR^{18}R^{19}$ or $NH_2$, wherein at least one of $R^2$ to $R^9$ is heterocyclic or aliphatic heterocyclic,
- $R^{18}$, $R^{19}$=H, a substituted or unsubstituted, aliphatic or aromatic hydrocarbon radical having from 1 to 25 carbon atoms, identical or different, and
- M=an alkali metal, an alkaline earth metal, ammonium or phosphonium ion.

12. The phosphinine-metal complex as claimed in claim 7, wherein W and X are each an aromatic hydrocarbon radical having from 1 to 50 carbon atoms and are covalently linked as in formula III

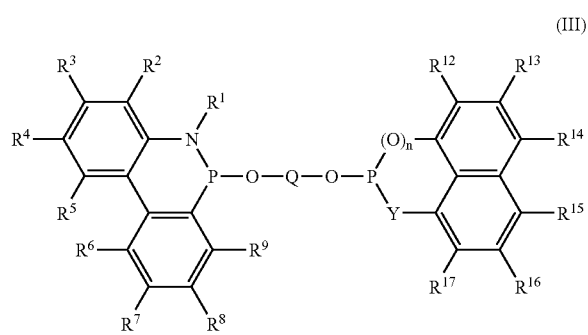

(III)

where
- $R^{12}$, $R^{13}$, $R^{14}$, $R^{15}$, $R^{16}$, $R^{17}$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where $R^{12}$ to $R^{17}$ are identical or different and may be covalently linked to one another, F, Cl, Br, I, —$CF_3$, —$OR^{18}$, —$COR^{18}$, —$CO_2R^{18}$, —$CO_2M$, —$SR^{18}$, —$SO_2R^{18}$, —$SOR^{18}$, —$SO_3R^{18}$, —$SO_3M$, —$SO_2NR^{18}R^{19}$, —$NR^{18}R^{19}$, $N{=}CR^{18}R^{19}$ or $NH_2$, wherein at least one of $R^2$ to $R^9$ is heterocyclic or aliphatic heterocyclic,
- $R^{18}$, $R^{19}$=H, a substituted or unsubstituted, aliphatic or aromatic hydrocarbon radical having from 1 to 25 carbon atoms, identical or different, and
- M=an alkali metal, an alkaline earth metal, ammonium or phosphonium ion.

13. The phosphinine-metal complex as claimed in claim 6, wherein W and X are each an aromatic hydrocarbon radical having from 1 to 50 carbon atoms and are covalently linked as in formula IV

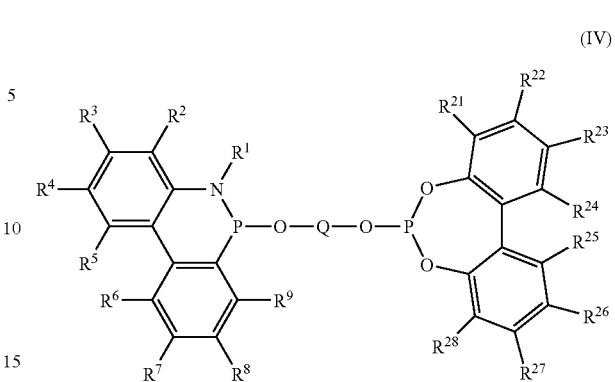

(IV)

where
- $R^{21}$, $R^{22}$, $R^{23}$, $R^{24}$, $R^{25}$, $R^{26}$, $R^{27}$, $R^{28}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, where $R^{21}$ to $R^{28}$ are identical or different and may be covalently linked to one another, F, Cl, Br, I, —$CF_3$, —$OR^{29}$, —$COR^{29}$, —$CO_2R^{29}$, —$CO_2M$, —$SR^{29}$, —$SO_2R^{29}$, —$SOR^{29}$, —$SO_3R^{29}$, —$SO_3M$, —$SO_2NR^{29}R^{30}$, —$NR^{29}R^{30}$, $N{=}CR^{29}R^{30}$ or $NH_2$,
- $R^{29}$, $R^{30}$=H, a substituted or unsubstituted, aliphatic or aromatic hydrocarbon radical having from 1 to 25 carbon atoms, and
- M=an alkali metal, an alkaline earth metal, ammonium or phosphonium ion.

14. The phosphinine-metal complex as claimed in claim 7, wherein W and X are each an aromatic hydrocarbon radical having from 1 to 50 carbon atoms and are covalently linked as in formula IV

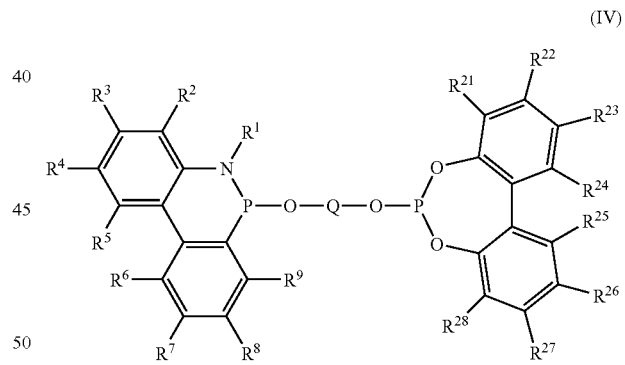

(IV)

where
- $R^{21}$, $R^{22}$, $R^{23}$, $R^{24}$, $R^{25}$, $R^{26}$, $R^{27}$, $R^{28}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, where $R^{21}$ to $R^{28}$ are identical or different and may be covalently linked to one another, F, Cl, Br, I, —$CF_3$, —$OR^{29}$, —$COR^{29}$, —$CO_2R^{29}$, —$CO_2M$, —$SR^{29}$, —$SO_2R^{29}$, —$SOR^{29}$, —$SO_3R^{29}$, —$SO_3M$, —$SO_2NR^{29}R^{30}$, —$NR^{29}R^{30}$, $N{=}CR^{29}R^{30}$ or $NH_2$,
- $R^{29}$, $R^{30}$=H, a substituted or unsubstituted, aliphatic or aromatic hydrocarbon radical having from 1 to 25 carbon atoms, and
- M=an alkali metal, an alkaline earth metal, ammonium or phosphonium ion.

15. The phosphinine-metal complex as claimed in claim 6, wherein W and X are each an aromatic hydrocarbon radical having from 1 to 50 carbon atoms and are covalently linked as in formula V

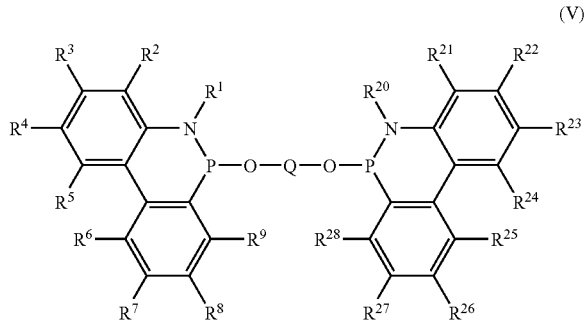

(V)

where
R$^{20}$=H, an aliphatic or aromatic hydrocarbon radical having from 1 to 25 carbon atoms,
R$^{21}$, R$^{22}$, R$^{23}$, R$^{24}$, R$^{25}$, R$^{26}$, R$^{27}$, R$^{28}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, where R$^{21}$ to R$^{28}$ are identical or different and may be covalently linked to one another, F, Cl, Br, I, —CF$_3$, —OR$^{29}$, —COR$^{29}$, —CO$_2$R$^{29}$, —CO$_2$M, —SR$^{29}$, —SO$_2$R$^{29}$, —SOR$^{29}$, —SO$_3$R$^{29}$, —SO$_3$M, —SO$_2$NR$^{29}$R$^{30}$, —NR$^{29}$R$^{30}$, —N=CR$^{29}$R$^{30}$ or NH$_2$,
R$^{29}$, R$^{30}$=H, a substituted or unsubstituted, aliphatic or aromatic hydrocarbon radical having from 1 to 25 carbon atoms,
M=an alkali metal, an alkaline earth metal, ammonium or phosphonium ion.
R$^2$ to R$^9$ are indentical or different and may be covalenty linked to one another.

16. The phosphinine-metal complex as claimed in claim 7, wherein W and X are each an aromatic hydrocarbon radical having from 1 to 50 carbon atoms and are covalently linked as in formula V

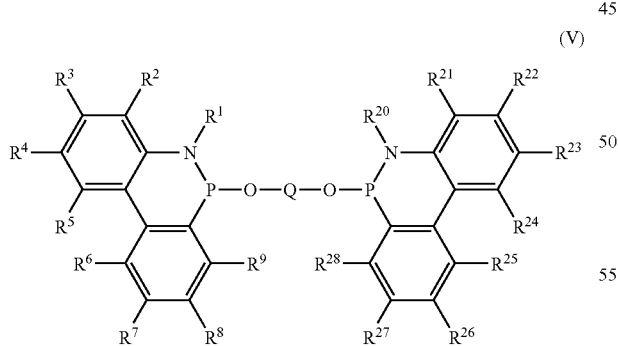

(V)

where
R$^{20}$=H, an aliphatic or aromatic hydrocarbon radical having from 1 to 25 carbon atoms,
R$^{21}$, R$^{22}$, R$^{23}$, R$^{24}$, R$^{25}$, R$^{26}$, R$^{27}$, R$^{28}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, where R$^{21}$ to R$^{28}$ are identical or different and may be covalently linked to one another, F, Cl, Br, I, —CF$_3$, —OR$^{29}$, —COR$^{29}$, —CO$_2$R$^{29}$, —CO$_2$M, —SR$^{29}$, —SO$_2$R$^{29}$, —SOR$^{29}$, —SO$_3$R$^{29}$, —SO$_3$M, —SO$_2$NR$^{29}$R$^{30}$, —NR$^{29}$R$^{30}$, —N=CR$^{29}$R$^{30}$ or NH$_2$,
R$^{29}$, R$^{30}$=H, a substituted or unsubstituted, aliphatic or aromatic hydrocarbon radical having from 1 to 25 carbon atoms,
M=an alkali metal, an alkaline earth metal, ammonium or phosphonium ion.
R$^2$ to R$^9$ are identical or different and may be covalently linked to one another.

17. The phosphinine-metal complex as claimed in claim 6, wherein Q is a hydrocarbon radical of the formula VI

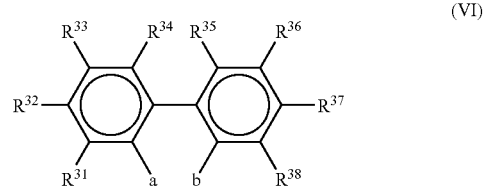

(VI)

where
R$^{31}$, R$^{32}$, R$^{33}$, R$^{34}$, R$^{35}$, R$^{36}$, R$^{37}$, R$^{38}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, F, Cl, Br, I, —CF$_3$, —OR$^{39}$, —COR$^{39}$, —CO$_2$R$^{29}$, —CO$_2$M, —SR$^{39}$, —SO$_2$R$^{39}$, —SOR$^{39}$, —SO$_3$R$^{39}$, —SO$_3$M, —SO$_2$NR$^{39}$R$^{40}$, —NR$^{39}$R$^{40}$, N=CR$^{39}$R$^{40}$ or NH$_2$,
R$^{39}$, R$^{40}$=H, a substituted or unsubstituted, aliphatic or aromatic hydrocarbon radical having from 1 to 25 carbon atoms, and
M=an alkali metal, an alkaline earth metal, ammonium or phosphonium ion, and where positions a and b serve as linkage points.

18. The phosphinine-metal complex as claimed in claim 8, wherein Q is a hydrocarbon radical of the formula VI

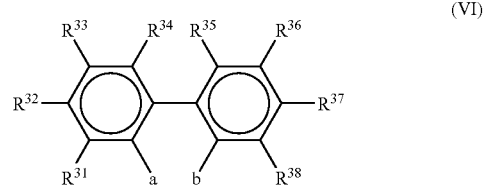

(VI)

where
R$^{31}$, R$^{32}$, R$^{33}$, R$^{34}$, R$^{35}$, R$^{36}$, R$^{37}$, R$^{38}$=H, an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, F, Cl, Br, I, —CF$_3$, —OR$^{39}$, —COR$^{39}$, —CO$_2$R$^{29}$, —CO$_2$M, —SR$^{39}$, —SO$_2$R$^{39}$, —SOR$^{39}$, —SO$_3$R$^{39}$, —SO$_3$M, —SO$_2$NR$^{39}$R$^{40}$, —NR$^{39}$R$^{40}$, N=CR$^{39}$R$^{40}$ or NH$_2$,
R$^{39}$, R$^{40}$=H, a substituted or unsubstituted, aliphatic or aromatic hydrocarbon radical having from 1 to 25 carbon atoms, and
M=an alkali metal, an alkaline earth metal, ammonium or phosphonium ion, and where positions a and b serve as linkage points.

19. The phosphinine-metal complex as claimed in claim 6, wherein the metal is rhodium, platinum, cobalt or ruthenium.

20. The phosphinine-metal complex as claimed in claim 7, wherein the metal is rhodium, platinum, cobalt or ruthenium.

21. The phosphinine-metal complex as claimed in claim 8, wherein the metal is rhodium, platinum, cobalt or ruthenium.

22. A process, comprising:

hydroformylating an olefin in a reaction medium containing a phosphinine having formula I

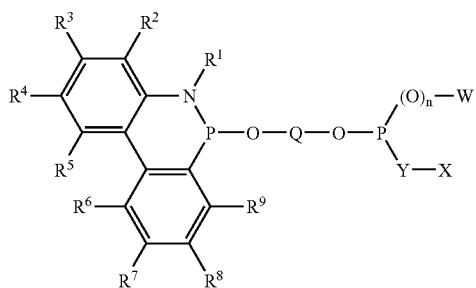

where n=0 or 1,

Y=O, NH, $NR^1$, $R^1$=H, an aliphatic or aromatic hydrocarbon radical having from 1 to 25 carbon atoms, $R^2$, $R^3$, $R^4$, $R^5$, $R^6$, $R^7$, $R^8$, $R^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where $R^2$ to $R^9$ are identical or different and may be covalently linked to one another, F, Cl, Br, I, —$CF_3$, —$OR^{10}$, —$COR^{10}$, —$CO_2R^{10}$, —$CO_2M$, —$SR^{10}$, —$SO_2R^{10}$, —$SOR^{10}$, —$SO_3R^{10}$, —$SO_3M$, —$SO_2NR^{10}R^{11}$, —$NR^{10}R^{11}$, N=$CR^{10}R^{11}$ or $NH_2$, $R^{10}$, $R^{11}$=H, a substituted or unsubstituted aliphatic or aromatic hydrocarbon radical having from 1 to 25 carbon atoms, identical or different, M=an alkali metal, an alkaline earth metal, ammonium or phosphonium ion, Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

23. A process, comprising:

hydroformylating an olefin in a reaction medium containing a phosphinine-metal complex as a catalyst, said phosphinine having formula I

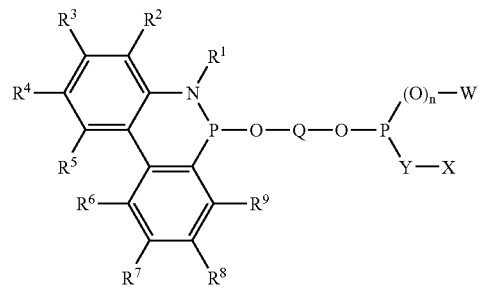

where n=0 or 1,

Y=O, NH, $NR^1$, $R^1$=H, an aliphatic or aromatic hydrocarbon radical having from 1 to 25 carbon atoms, $R^2$, $R^3$, $R^4$, $R^5$, $R^6$, $R^7$, $R^8$, $R^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where $R^2$ to $R^9$ are identical or different and may be covalently linked to one another, F, Cl, Br, I, —$CF_3$, —$OR^{10}$, —$COR^{10}$, —$CO_2R^{10}$, —$CO_2M$, —$SR^{10}$, —$SO_2R^{10}$, —$SOR^{10}$, —$SO_3R^{10}$, —$SO_3M$, —$SO_2NR^{10}R^{11}$, —$NR^{10}R^{11}$, N=$CR^{10}R^{11}$ or $NH_2$, $R^{10}$, $R^{11}$=H, a substituted or unsubstituted aliphatic or aromatic hydrocarbon radical having from 1 to 25 carbon atoms, identical or different, M=an alkali metal, an alkaline earth metal, ammonium or phosphonium ion, Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

24. A process, comprising:

hydroformylating an olefin in a reaction medium, wherein said phosphinine having the following formula I and at least one other phosphorus containing ligand are present in the olefin

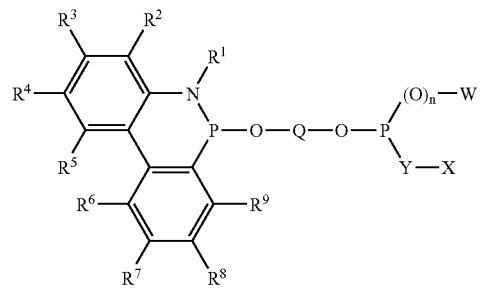

where n=0 or 1,

Y=O, NH, NR$^1$,

R$^1$=H, an aliphatic or aromatic hydrocarbon radical having from 1 to 25 carbon atoms, R$^2$, R$^3$, R$^4$, R$^5$, R$^6$, R$^7$, R$^8$, R$^9$=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$, R$^{10}$, R$^{11}$=H, a substituted or unsubstituted aliphatic or aromatic hydrocarbon radical having from 1 to 25 carbon atoms, identical or different, M=an alkali metal, an alkaline earth metal, ammonium or phosphonium ion, Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

25. A process, comprising:

hydroformylating an olefin in a reaction medium containing a phosphinine-metal complex as a catalyst, said phosphinine having formula I

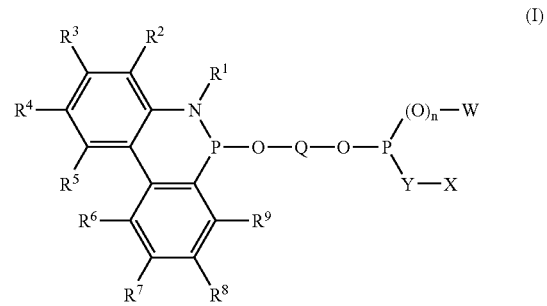

(I)

where n=0 or 1,

Y=O, NH, NR$^1$,

R$^1$=H, an aliphatic or aromatic hydrocarbon radical having from 1 to 25 carbon atoms, R$^2$, R$^3$, R$^4$, R$^5$, R$^6$, R$^7$, R$^8$, R$^9$,=H, an aliphatic, alicyclic, aliphatic-alicylic, heterocyclic, aliphatic-heterocyclic, aromatic, aromatic-aromatic, or aliphatic-aromatic hydrocarbon radical having from 1 to 50 carbon atoms, where R$^2$ to R$^9$ are identical or different and may be covalently linked to one another, F, Cl, Br, I, —CF$_3$, —OR$^{10}$, —COR$^{10}$, —CO$_2$R$^{10}$, —CO$_2$M, —SR$^{10}$, —SO$_2$R$^{10}$, —SOR$^{10}$, —SO$_3$R$^{10}$, —SO$_3$M, —SO$_2$NR$^{10}$R$^{11}$, —NR$^{10}$R$^{11}$, N=CR$^{10}$R$^{11}$ or NH$_2$, R$^{10}$, R$^{11}$=H, a substituted or unsubstituted aliphatic or aromatic hydrocarbon radical having from 1 to 25 carbon atoms, identical or different, M=an alkali metal, an alkaline earth metal, ammonium or phosphonium ion, Q=a divalent aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, and W and X are each an aliphatic, alicyclic, aliphatic-alicylic, heterocyclic, aliphatic-heterocyclic, aromatic, aromatic-aromatic or aliphatic-aromatic hydrocarbon radical having from 1 to 50 carbon atoms, which may be identical or different or covalently linked to one another.

* * * * *